(12) United States Patent
Koh et al.

(10) Patent No.: US 9,371,269 B2
(45) Date of Patent: *Jun. 21, 2016

(54) METHOD FOR PREPARING DIALKYL CARBONATE

(71) Applicant: RESEARCH INSTITUTE OF INDUSTRIAL SCIENCE & TECHNOLOGY, Pohang (KR)

(72) Inventors: Jae Cheon Koh, Daejeon (KR); Chul Ung Kim, Daejeon (KR); Yun Min Kim, Daejeon (KR)

(73) Assignee: RESEARCH INSTITUTE OF INDUSTRIAL SCIENCE & TECHNOLOGY, Pohang (KR)

( * ) Notice: Subject to any disclaimer, the term of this patent is extended or adjusted under 35 U.S.C. 154(b) by 201 days.

This patent is subject to a terminal disclaimer.

(21) Appl. No.: 14/100,078

(22) Filed: Dec. 9, 2013

(65) Prior Publication Data

US 2014/0094621 A1   Apr. 3, 2014

Related U.S. Application Data

(63) Continuation of application No. 13/388,078, filed as application No. PCT/KR2009/006726 on Nov. 27, 2009, now Pat. No. 8,629,295.

(30) Foreign Application Priority Data

Jul. 31, 2009   (KR) .......................... 10-2009-0070891

(51) Int. Cl.
   *C07C 68/00*   (2006.01)

(52) U.S. Cl.
   CPC ..................................... *C07C 68/00* (2013.01)

(58) Field of Classification Search
   None
   See application file for complete search history.

(56) References Cited

FOREIGN PATENT DOCUMENTS

| JP | 2000-128834 | 5/2000 |
| JP | 2005-206503 | 8/2005 |
| JP | 2006-061905 | 3/2006 |
| WO | 2005/033060 | 4/2005 |

OTHER PUBLICATIONS

Hong Wang et al., "Highly selective synthesis of dimethyl carbonate from urea and methanol catalyzed by ionic liquids", Fuel Processing Technology, 2009, vol. 90, pp. 1198-1201.

*Primary Examiner* — Rebecca Anderson
*Assistant Examiner* — Po-Chih Chen
(74) *Attorney, Agent, or Firm* — Lex IP Meister, PLLC

(57) ABSTRACT

The present invention provides a method for preparing dialkyl carbonate from urea or alkyl carbamate and alkyl alcohol using an ionic liquid comprising a cation, which produces a hydrogen ion, and a hydrophobic anion containing fluorine with high temperature stability in the presence of catalyst containing a metal oxide or hydrotalcite. Since the present invention can prepare dialkyl carbonate at a pressure lower than those of existing methods, it does not require an expensive pressure control device and peripheral devices for maintaining high pressure including the installation cost. It is also the method for preparing a dialkyl carbonate with high yield, thus improving economical efficiency. Moreover, the method of the present invention hardly produces any waste during the process and is thus an eco-friendly method.

20 Claims, No Drawings

METHOD FOR PREPARING DIALKYL CARBONATE

TECHNICAL FIELD

The present invention relates to a method for preparing dialkyl carbonate from urea or alkyl carbamate and alkyl alcohol using a metal oxide catalyst and an ionic liquid comprising a cation, which produces a hydrogen ion, and a hydrophobic anion containing fluorine with high temperature stability.

BACKGROUND ART

Dimethyl carbonate (hereinafter 'DMC'), a typical dialkyl carbonate, is colorless, odorless and has an environment-friendly molecular structure without any known toxicity to human body. Since DMC contains highly reactive groups of methoxy group, carbonyl group and carbonyl methyl oxygen group in its molecule structure, it can be used to replace highly toxic phosgene as carbonylating agent and also dimethyl sulfate and methyl halides as methylating agent.

DMC has an excellent solubility and is thus used as an environment-friendly solvent to replace halogenated solvents such as chlorobenzene. It has been widely used as a substitute for phosgene as a raw material for polycarbonate, an additive for improving the octane number of automotive fuel, and an electrolyte for rechargeable batteries.

DMC has been mainly synthesized by methanol and phosgene in the presence of highly concentrated sodium hydroxide solution. High toxicity of phosgene and corrosiveness of chlorine ion have been limiting a large-scale production of DMC and its applications.

In 1983, Enichem Company in Italy developed a non-phosgene method to synthesize DMC by oxidative carbonylation of methanol and carbon monoxide with oxygen in the presence of a monovalent copper chloride catalyst. However, this method has some problems such as use of a toxic carbon monoxide as a raw material, a low conversion rate and a high energy cost due to unreacted methanol and by-product water. Further, because the copper chloride (I) catalyst is readily oxidized to a divalent copper ion, its catalytic activity is reduced. Further, it also requires continued monitoring of the reaction chamber against the corrosion and explosion. In addition, due to the presence of a small amount of chloride ions in the product, the refining cost is considerably increased when DMC is used as an electrolytic solution in a secondary lithium battery.

Another conventional method for preparing DMC is Ube process. The process proceeds in two steps in gas-phase: in the first step, methanol reacts with nitrogen oxide (NO) and oxygen to give methylnitrite (MN) and water, without any catalyst. In the second step, MN reacts with carbon monoxide to produce DMC, in the presence of a palladium supported catalyst. In the catalytic process, the NO produced in the latter reaction is converted again to MN. Although the cost of energy for the separation and purification process is relatively low in this process, the use of the highly toxic and corrosive carbon monoxide and NO requires an anti-corrosion reaction chamber, an anti-explosion safety device for a precise controlling of raw materials concentration. Also, there is a problem that the reactants may leak.

Still another conventional method for preparing DMC is Texaco process in which ethylene oxide (or propylene oxide) and carbon dioxide are reacted with each other at high pressure in the presence of a catalyst to form ethylene carbonate (or propylene carbonate) and thus prepared DMC and ethylene glycol (propylene glycol) through ester interchange reaction with methanol Unlike the above-mentioned two conventional processes, the Texaco process does not use carbon monoxide and is thus considered a very safe process. However, since the process is performed at high temperature and pressure, there is still a possibility of explosion due to leakage of ethylene oxide. Moreover, the conversion rate is not very high, and thus it still requires a large amount of energy for the separation and purification of DMC and ethylene glycol as products from unreacted materials.

Yet still another method for preparing DMC is a method for directly synthesizing carbon dioxide and methanol at high temperature and pressure in the presence of a catalyst. However, the yield of DMC is extremely low in a thermodynamic equilibrium state Recently, a method for preparing dialkyl carbonate by directly synthesizing urea and methanol in the presence of a catalyst has been actively studied. This method has the advantages that inexpensive urea is used as a raw material and, since water is not produced as a by-product, a ternary azeotropic mixture such as methanol-water-DMC is not formed, thus simplifying the separation and purification process. Moreover, the ammonia produced as a by-product can be reused by a urea formation by synthesizing ammonia with carbon dioxide, and thus it is possible to provide an environment-friendly process which does not produce by-products.

The methods for preparing DMC from urea and methanol are as follows. Method (1) for synthesizing DMC from urea and methanol in the presence of a zinc acetate catalyst (S. Bowden., E. Buther, J. Chem. Soc. 1939, vol. 78) and method (2) for synthesizing various dialkyl carbonates from urea and primary aliphatic alcohol in the presence of an organic metal compound catalyst such as magnesium methoxide [$Mg(OCH_3)_2$] and an organic phosphine catalyst such as triphenylphosphine ($PPh_3$) (Peter Ball, Heinz Fullmann, and Walter Heintz, "Carbonates and Polycarbonates from Urea and Alcohol", Angrew. Chem. Int. Ed. Engl. 1980, vol. 19, No. 9, pp 718-720, WO 95/17369). However, the above conventional methods (1) and (2) for preparing DMC have the problem that the yield is low.

Another method (3) for preparing DMC in the presence of a catalyst complex comprising an organotin compound and a high boiling electron donor compound containing polyglycol ether such as triethylene glycol dimethyl ether (PGDE) is disclosed in U.S. Pat. No. 6,010,976 by J Yong Rye, and various process patents are disclosed in U.S. Pat. No. 6,392,078 B1 and U.S. Pat. No. 7,314,947 B2 based on method (3). However, the disclosed catalyst complex has the disadvantages that the catalytic activity is rapidly reduced by water contained in a raw material as an impurity and it has toxicity to the ecosystem. Moreover, the high boiling oxygen containing polyglycol ether compound used as a co-catalyst is decomposed or polymerized at high temperature, and thus the activity of the co-catalyst is reduced due to the change in viscosity by thermal decomposition. Further, the organotin catalyst and the polyglycol ether compound used as co-catalyst are to be discarded due to the difficulty in their recycling, and this raises an environmental issue.

There is another method (4) for preparing DMC by directly reacting urea with methanol in a catalyst rectification reactor or distillation column using alumina and silica supports on which metal oxides such as Zn, Pb, Mn, La, and Ce and alkali oxides such as K, Na, Cs, Li, Ca, and Mg are impregnated as reaction catalysts (U.S. Pat. No. 7,271,120). This method is an improved method that can easily separate a catalyst from a given product. However, because the reaction temperature is much higher than the boiling point of methanol, it is necessary to maintain the vapor-liquid equilibrium at high pressure. Moreover, if the produced ammonia and DMC) are not discharged, the reaction yield is reduced, and the amount of by-products such as N-methyl carbamate (N-MC) and N,N-dimethyl carbamate (NN-DMC) is increased due to a side reaction between methyl carbamate (MC) as an intermediate product and DMC. Therefore, in order to improve the reaction yield and distillation efficiency of DMC at the reaction temperature higher than the boiling point of methanol and under the high vapor pressure of methanol during the preparation of DMC by the reactive distillation. It is necessary to maintain the reaction temperature and the pressure at the vapor-liquid equilibrium and it is further necessary to discharge ammonia and distillate to obtain DMC.

Here, the distillate is obtained as an azeotropic mixture of DMC and methanol, and the concentration of DMC in the azeotropic mixture is reduced at high pressure, which reduces the productivity. Although the amount of by-products in method (4) is smaller than that of method (3), the amount of by-products such as N-MC and NN-DMC is increased due to a high reactivity of the synthesized DMC which is reacted with MC as an intermediate product at high pressure as represented by the following reaction scheme, which is well-known in the art (Yoshio Ono, "Dimethyl carbonate for environmentally benign reaction", Pure & Appl. Chem., 1996, Vol. 68, No. 2, pp 367-375).

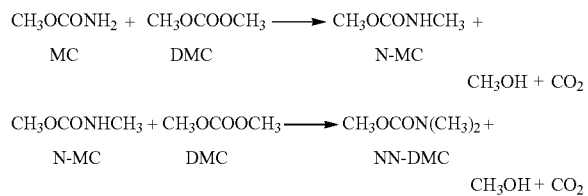

In addition, the method (5) for preparing DMC using polyethylene glycol dimethyl ether (PGDE, MW 250 to 270) as an organic solvent, which is stable at atmospheric pressure and reaction temperature, while inhibiting the decomposition of urea and MC in the presence of various metal catalysts is disclosed (Bolin Yang et al. "Synthesis of dimethyl carbonate from urea and methanol catalyzed by the metallic compounds at atmospheric pressure", Catalysis communications, 2006, vol. 7, p. 472-477). PGDE used is an organic solvent used as a medium for maintaining the reaction temperature at atmospheric pressure and as an electron donor or used to inhibit the decomposition of raw materials. However, this method has also some problems such as recycling of used PGDE and catalysts due to decomposition, consumption during reaction and low yield per unit time.

Moreover, a method (6) for preparing dialkyl carbonate by the reaction of urea or alkyl carbamate and alkyl alcohol using a quaternary ammonium ionic liquid such as tetramethylammonium hydrogencarbonate methyl ester and tetramethylammonium carbamate and an organotin catalyst at a temperature of 160° C. and a pressure of 20 atmospheres is disclosed in U.S. Pat. No. 5,534,649. However, method (6) for preparing DMC using methyl carbamate, methanol, and an ionic liquid has the problem that the maximum yield of DMC is very low (4.13%).

In general, the reaction process of synthesizing dialkyl carbonate by the reaction of alkyl alcohol and urea can be represented by the following reaction scheme 1:

<Reaction Scheme 1>

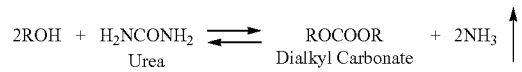

It can be seen from the above reaction scheme 1 that when the produced dialkyl carbonate and ammonia are effectively discharged from the reactor, the equilibrium reaction will shift to the forward direction, thereby increasing the reaction rate and yield. In the synthesis of DMC, due to the low boiling point of methyl alcohol as a reactant, it is necessary to increase the reaction pressure (15 to 25 atmospheres) in order to maintain the reaction temperature, and thus the solubility of dialkyl carbonate and ammonia produced at high pressure is increased. As a result, the equilibrium constant becomes low, thereby reducing the reaction rate and yield. Moreover, since the solubility of DMC produced at high pressure is also increased, the amount of undesired by-products such as N-MC and NN-DMC is increased.

DISCLOSURE OF INVENTION

Technical Problem

Technical problems on conventional methods are limitations on a large-scale production and applications due to high toxicity of phosgene, carbon monoxide and corrosiveness of chlorine ion, low conversion rate and a high energy cost due to unreacted methanol and by-product water.

Although the cost of energy for the separation and purification is relatively low in some processes, there are still some disadvantages such as the use of the highly toxic and corrosive carbon monoxide and NO requires an anti-corrosion reaction chamber, an anti-explosion safety device for preventing reactants leakage.

A direct synthesizing method of DMC using carbon dioxide and methanol also has some disadvantages such as the low yield of DMC due to a thermodynamic equilibrium state at high temperature and pressure.

In addition, the method for preparing DMC using an organotin catalyst and polyethylene glycol dimethyl ether (PGDE, MW 250 to 270) as an high temperature organic solvent as co-catalyst, which has the disadvantages that the catalytic activity is rapidly reduced by water and high toxicity. Moreover, the high boiling oxygen containing polyglycol ether is decomposed or polymerized at high temperature, and thus the activity of the co-catalyst is reduced due to the change in viscosity by thermal decomposition.

Solution to Problem

To accomplish the above objects of the present invention, there is provided a method for preparing dialkyl carbonate from urea or alkyl carbamate and alkyl alcohol using an ionic liquid comprising a cation, which produces a hydrogen ion (H$^+$), and a hydrophobic anion containing fluorine and a catalyst containing at least one selected from the group consisting of an alkali earth metal oxide, a transition metal oxide, a rare earth oxide, and a hydrotalcite. Therefore, an object of the present invention is to provide a new method for preparing dialkyl carbonate from urea or alkyl carbamate and alkyl alcohol using an ionic liquid at low pressure.

Advantageous Effects of Invention

Since the ionic liquid used in the present invention has excellent stability by contact with water and air, it does not flow out with the reaction products during the reaction. Moreover, since the ionic liquid can easily dissolve urea as a raw material and alkyl carbamate as an intermediate product, it is possible to maintain a high concentration of raw material without decomposition and sublimation at high temperature, thereby increasing the reaction rate. Also, it is possible to prevent the generation of by-products and increase the productivity due to the increase of activity of the metal oxide catalyst even at high temperature and low pressure. Therefore, the present invention is an environment-friendly preparation method that significantly reduces the amount of energy used and produces no waste. Especially by adapting low pressure distillation, it will increase the concentration of the product at the azeotropic point. The amount of alkyl alcohol as a circulating raw material is also reduced, which reduces the size of the apparatus while improving its productivity. Further, the present invention enables to increase the reuse of the ionic liquid and catalyst including the high yield of dialkyl carbonate.

Mode for the Invention

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

A method for preparing dialkyl carbonate by reacting alkyl alcohol with urea or alkyl carbamate in the presence of:

an ionic liquid comprising a cation capable of generating a hydrogen ion (H±), and a hydrophobic anion containing fluorine, and a catalyst comprising at least one selected from the group consisting of an alkali earth metal oxide, a transition metal oxide, a rare earth oxide, and a hydrotalcite.

In particular, the present invention aims at preparing dialkyl carbonate by reacting urea and alkyl alcohol under atmospheric pressure and at a temperature of 140 to 240° C., preferably 150 to 220° C. If the reaction temperature is below 140° C., the reaction rate is significantly reduced, whereas if it exceeds 240° C., the amount of by-products is significantly increased. Thus, it is preferable that the reaction is performed in the above temperature range.

Moreover, the method for preparing dialkyl carbonate does not require high pressure corresponding to the vapor pressure of alkyl alcohol (15 to 25 atm in the case of methanol) depend on the reaction temperature required in the existing preparation methods. The method for manufacturing dialkyl carbonate of the present invention can be carried out at low pressure as well as at high pressure, preferably at a pressure of 0.1 to 1.5 atm, more preferably at atmospheric pressure, through product recycling process including methyl alcohol. However, unlike the conventional methods, the method according to the present invention enables to manufacture dialkyl carbonate at any pressure regardless of the vapor pressure of alkyl alcohol and thus the present invention is not limited thereto.

The ionic liquid used in the present invention is in the form of [cation][anion] pairs and serves as a solvent and a heat medium capable of maintaining urea and methyl carbamate as an intermediate product in a liquid form at high temperature and low pressure. Moreover, the ionic liquid produces hydrogen ions to improve the reaction rate of the catalyst. Further, since the ionic liquid easily dissolves urea as a reactant, it is possible to increase the concentration of urea. In addition, the ionic liquid is not decomposed at the reaction temperature and has no reactivity with alkyl alcohol, ammonia, and water as a reactant.

The [cation] is a cation which produces a hydrogen ion ($H^+$), preferably a cation which produces a hydrogen ion ($H^+$) and contains at least one substituent selected from the group consisting of a $C_1$-$C_{16}$ hydroxyalkyl group, a $C_1$-$C_{16}$ alkoxy group, and a $C_1$-$C_{16}$ alkyl group. The N-substituent s backbone may comprise a quaternary ammonium cation, an imidazolium cation, a pyridium cation, a pyrazolium cation, a pyrrolinium cation, a quaternary phosphonium cation, a thiazolium cation, or a sulfonium cation, preferably a quaternary ammonium cation, an imidazolium cation, a pyridium cation, or a pyrazolium cation. Here, if the carbon number of the substituent exceeds 16, the ionic liquid may have a melting point higher than the reaction temperature regardless of the anion. Thus, it is preferable that the substituent has the above number of carbon atoms. Moreover, it is preferable to use an ionic liquid which hash has a melting point lower than the reaction temperature, and more preferably an ionic liquid which is a liquid at room temperature (i.e., a room temperature ionic liquid). However, the carbon number is not particularly limited in the present invention.

The [cation] will be described in more detail below. The quaternary ammonium cation may have at least one substituent selected from the group consisting of a $C_1$-$C_{16}$ hydroxyalkyl group, a $C_1$-$C_{16}$ alkoxy group, and a $C_1$-$C_{16}$ alkyl group. Preferably, the quaternary ammonium cation may have at least one substituent selected from the group consisting of a $C_1$-$C_5$ hydroxyalkyl group, a $C_1$-$C_5$ alkoxy group, and a $C_1$-$C_5$ alkyl group. More preferably, the quaternary ammonium cation may be a hydroxymethyltrimethylammonium cation ($(CH_3)_3N^+CH_2OH$), a hydroxyethyltrimethylammonium cation ($(CH_3)_3N^+C_2H_4OH$, choline), a hydroxyethyltriethylammonium cation [$(CH_2H_5)_3N^+C_2H_4OH$], a hydroxyethyltripropylammonium cation [$(C_3H_7)_3N^+C_2H_4OH$], a hydroxyethyltributylammonium cation [$(C_4H_9)_3N^+C_2H_4OH$], a tetraethylammonium cation [$(C_2H_5)_4N^+$], or a tetrabutylammonium cation[$(C_4H_9)_4N^+$]. The imidazolium cation may have at least one substituent selected from the group consisting of a $C_1$-$C_{16}$ hydroxyalkyl group, a $C_1$-$C_{16}$ alkoxy group, and a $C_1$-$C_{16}$ alkyl group. More preferably, the imidazolium cation may be a 1,3-di($C_1$-$C_5$)alkyl-imidazolium cation or a 1-hydroxy($C_1$-$C_5$)alkyl-3-($C_1$-$C_5$)alkyl imidazolium cation. Moreover, the N-hydroxyalkylpyridium cation may be an N-hydroxy($C_1$-$C_{16}$)alkylpyridinium cation, preferably an N-hydroxy($C_1$-$C_3$)alkylpyridinium cation. The pyrazolium cation may be a 1-hydroxy($C_1$-$C_{16}$)alkyl-2-($C_1$-$C_{16}$)alkylpyrazolium cation, preferably a 1-hydroxy($C_1$-$C_5$)alkyl-2-($C_1$-$C_5$)alkylpyrazolium cation.

The [anion] of the ionic liquid may be a compound containing fluorine for the good stability at high temperature and in water. The anion may be bis(trifluoromethylsulfonyl)imide ($NTf_2$), trifluoromethanesulfonate (OTf), tris(trifluoromethylsulfonyl)methanide, ($CTf_3$). However, in the case where a halogen anion ($F^-$, $Cl^-$, $Br^-$, or $I^-$) is used as the anion, the melting point of the ionic liquid is too high, the thermal stability is low, and the solubility to water is increased. As a result, it is difficult to recover the ionic liquid owing to an easy decomposed anion under the reaction temperature and reacted with a metal oxide catalyst to inhibit the activity of the catalyst. Moreover, in the case of tetrafluoroborate (BR) or hexafluorophosphate ($PF_6$), it reacts with alkyl alcohol as a reactant to produce by-products such as trialkoxyboroxane and alkoxy phosphorus compounds or generate hydrofluoric acid (HF), which causes corrosion to a reactor.

In the present invention, the catalyst may be at least one selected from the group consisting of an alkali earth metal oxide, a transition metal oxide, a rare earth oxide. Moreover, the catalyst may be impregnated onto a support such as silica, alumina, titania, zirconia or ceria. Further, the catalyst may be a mixed oxide with a crystalline composite oxide such as hydrotalcite. Examples of the alkali earth metal oxide, the transition metal oxide, the rear earth oxide include CaO, MgO, ZnO, CuO, PbO, $La_2O_3$, $Y_2O_3$ which can be impregnated onto a support. Although the size of the catalyst is not particularly limited, the reaction rate is increased and the yield is improved when a nano-sized catalyst is used. The amount of catalyst used is preferably 1 to 10 parts by weight per 100 parts by weight of the ionic liquid. If the amount of catalyst used is less than 1 part by weight, the reaction rate and DMC yield are decreased, respectively. Meanwhile, if it exceeds 10 parts by weight, the yield improvement effect by an increase in the amount of catalyst used is reduced due to an increase in viscosity, which is uneconomic.

The hydrotalcite may be a mixed oxide prepared by drying or calcining powder having a structure of $Mg_xAl_y(OH)_{2(x+y)}(CO_3)_{y/2} \cdot mH_2O$. In the structure of the hydrotalcite, the ratio of x/y may be in the range of 3 to 9, and m represents the number of water for crystals. It is preferable that the hydrotalcite is completely dried at a temperature above 120° C. to prevent the decomposition of urea into ammonia and carbon dioxide by the reaction with water in the hydrotalcite. It is more preferable that the hydrotalcite is calcined at a temperature above 400° C. to be a mixed oxide of magnesium and alumina to prevent the decomposition of urea, thus increasing the yield.

The alkyl alcohol as a main raw material for the preparation of dialkyl carbonate may be a linear, branched, or cyclic alkyl alcohol, preferably, but not particularly limited to, $C_1$-$C_6$ alkyl alcohol in terms of reactivity; however, the present invention is not limited thereto. The alkyl alcohol may be fed through a conduit at a constant flow rate of 0.1 to 10 ml/min relative to 100 parts by weight of the ionic liquid, preferably at a constant flow rate of 0.1 to 5 ml/min. If the flow rate of the alkyl alcohol is less than 0.1 ml/min, the productivity is reduced, whereas if it exceeds 10 ml/min, it is difficult to control the reaction temperature due to the heat of vaporization of alkyl alcohol. Moreover, the increase in the amount of unreacted urea and alkyl alcohol leads to generation of a condensate with a low-concentrated dialkyl carbonate, and increases the cost for purifying dialkyl alcohol, thus being commercially not advantageous. It is still possible to increase the reaction yield by controlling the form of the reactor, the disperser of alkyl alcohol, and the stirring rate to increase the flow rate of alkyl alcohol, and thus the present invention is not limited to the flow rate.

The amount of urea or alkyl carbamate as a main raw material for the preparation of dialkyl carbonate may be 1 to 30 parts by weight per 100 parts by weight of the ionic liquid, preferably 1 to 25 parts by weight. Moreover, the molar ratio of alkyl alcohol to urea or alkyl carbamate may be 5 to 30:1. If the molar ratio of alkyl alcohol to urea or alkyl carbamate is less than 5, the yield of dialkyl carbonate is reduced. Meanwhile, if it exceeds 30, a large amount of unreacted urea and methyl carbamate is distilled to reduce the selectivity, and the amount of alkyl alcohol recycled is increased, thus increasing the energy required for the recycling of alkyl alcohol. Therefore, the molar ratio of alkyl alcohol to urea or alkyl carbamate may be maintained within the above range, preferably 5 to 25:1, more preferably 5 to 20:1. Although the flow rate of alkyl alcohol to the reactor may differ according to the reactor and disperser type and the stirring rate, the alkyl alcohol is fed in 100 parts by weight of the ionic liquid at a flow rate of 0.1 to 10 ml/min, preferably at a flow rate of 0.25 to 5 ml/min, more preferably at a flow rate of 0.25 to 3 ml/min. If the flow rate of alkyl alcohol is less than 0.1 ml/min, the selectivity becomes good, but the reaction rate is reduced. Meanwhile, if the flow rate exceeds 5 ml/min, the selectivity is reduced, but the reaction rate is increased. However, the excessive feeding of alkyl alcohol may cause a problem in the control of the reaction temperature, and the energy required for the separation and purification is increased.

The alkyl of the alkyl carbamate may have a carbon number of 1 to 6, preferably 1 to 3, which is advantageous since there is no steric hindrance during reaction with alkyl alcohol can be used; however, the present invention is not limited thereto.

The ionic liquid and catalyst used in the present invention may be collected and recycled. The ionic liquid may be collected when the activity of the catalyst decreases or when the catalyst is contaminated. The catalyst as a form solid can be recovered using centrifugation or filtration.

The used ionic liquid contaminated with the carbonized organic materials may be decolorized by using activated carbon. Inorganic impurities such as metal oxides dissolved in the ionic liquid may be purified by a strong acid such that a metal salt solution of the upper layer is discarded. Thus obtained lower layer ionic liquid washed with some distilled water and further washed with ether if necessary. The purified ionic liquid is dried by the vacuum-rotary-evaporator and then reused. Therefore, the method for preparing dialkyl carbonate of the present invention is an environment-friendly method which does not discharge other waste.

Next, the present invention will be described in more detail with reference to Examples, but the scope of the present invention is not limited to the following Examples.

EXAMPLES

Synthesis Example

Synthesis of Ionic Liquid in the Form of [Choline][NTf$_2$]

139.82 g (1.0 mol) of choline chloride (2-hyrdoxyethyltrimethylammoniun chloride or vitamin B4; MW 139.82, mp 302 to 305° C.) dissolved in 250 ml of distilled water, mixed with 500 ml aqueous solution of 1.0 mol of lithium bis(trifluoromethylsulfonyl)imide ([Li][NTf$_2$], MW 287.08) in a 1 L beaker, stirred at room temperature for 4 hours, and left to stand for phase separation. The upper layer was discarded from the solution, and the remaining ionic liquid was washed with 200 ml of distilled water several times until no chloride ions (Cl$^-$) were detected by silver nitrate test in the washing solution. Upon completion of the purification, the resulting ionic liquid was placed in a rotary evaporator and vacuum-dried at 120° C. for more than 6 hours, thus removing water. As a result, 312.59 g of ionic liquid ($C_7H_{14}F_6N_2O_5S_2$ MW: 384.02) in the form of [Choline][NTf$_2$] was obtained at a yield of 81.4%. The [choline] was the 2-hydroxyethyltrimethylammonium cation, and the [NTf$_2$] was the bis(trifluoromethylsulfonyl)imide anion.

The moisture content measured by a Karl Fischer method was 0.493%. NMR results analyzed by $^1$H-NMR (300 MHz, d6-DMSO) were δ=3.099 (3xCH$_3$), 3.38 (O—CH$_2$—), 3.84 (N—CH$_2$—), and 5.25 (—OH) and the results analyzed by $^{13}$C-NMR (d6-DMSO) were δ=53.51 (CH$_2$—O), 55.50 (3xCH$_3$), 67.42 (N—CH$_2$—), and 120 (2xCF$_3$). The results of atomic analysis were C, 21.78%, H, 3.71%, N, 7.83%, and S, 17.58%, those were well agreed with the theoretical atomic ratios of [Choline] [NTf$_2$] (C$_7$H$_{14}$N$_2$O$_5$F$_6$S$_2$, MW; 384.02) are C, 21.88%, H, 3.67%, N, 7.29%, and S, 16.69%. Freezing point measured by differential scanning calorimetry (DSC) was −16° C., melting point was 1.0° C., and specific gravity of liquid at 29.3° C. was 1.520 g·cm$^{-3}$.

Example 1

Preparation of DMC at Atmospheric Pressure and 180° C.

A reaction system such as a distillation system equipped with a magnetic stirrer capable of stirring the mixture was used. A mantle type heater with temperature indicator and controller was used and was equipped with a condenser, an ammonia absorber, and a metering pump. Moreover, the reactor was connected to a metering pump capably of injecting alkyl alcohol at a constant flow rate into a reaction solution containing the ionic liquid and urea. A preheat coil capable of vaporizing the injected alkyl alcohol was installed in the reactor such that the alkyl alcohol was dispersed in the vapor phase to the reaction. When the reaction system was established, 100.08 g of ionic liquid [choline][NTf$_2$] synthesized in the above Synthesis Example and 7.502 g (0.125 mol) of urea were placed in a 250 ml three-necked round flask reactor and mixed with 2.003 g of zinc oxide used as a catalyst. Nitrogen was fed into the reactor to replace air, and the temperature of the reactor was increased to 180±1.0° C. During the reaction, a coolant was circulated to maintain the temperature of condenser at 5° C. When the reaction temperature was reached, the supply of nitrogen was cut off, and 60 g (1.873 mol) of methanol was fed into the reactor at a flow rate of 0.5 ml/min using a metering pump.

The above process was performed at about 1 atm (i.e., atmospheric pressure), and the sampling of the condensate in the condenser upon completion of 2.5 hours of the pure methanol feeding. Then, the sample collected again from the condensate after every 6.5 and 10.5 hours during the condensate was circulated at the same flow rate of 0.5 ml/min using the metering pump to continue the reaction. The samples were analyzed as shown in the following table 1.

When the reaction was continued for 10.5 hours, only MC as an impurity was present in the condensate. Meanwhile, only N-MC was present in the condensate and the yield was increased after 14.5 hours, the DMC yield gradually decreased and some kinds of impurities was appeared. The decrease in DMC yield appears to be due to side reaction of DMC to N-MC.

The reactants and products were analyzed by gas chromatography (GC) with an HP-5 capillary column (0.32 mm ID×30 m×1 μm) and an FID detector. The quantitative analysis of DMC was performed by external standard method using heptanol. Moreover, the yield and selectivity were obtained by the following formula 1 and 2, respectively. However, the amounts of dialkyl carbonate and the total product were calculated by analyzing the products collected from the condenser.

Math Figure 1

$$\text{Yield (\%)} = \frac{\text{Dialkyl Carbonate (mol)}}{\text{Urea (mol)}} \times 100 \ (\%) \quad \text{[Math. 1]}$$

Math Figure 2

$$\text{Selectivity (\%)} = \frac{\text{Dialkyl Carbonate (mol)}}{\text{Total product (mol)}} \times 100 \ (\%) \quad \text{[Math. 2]}$$

Example 1-1

DMC was prepared in the same manner as in Example 1, except that methyl carbamate was used instead of urea.

Examples 2 to 9

Preparation of DMC at Atmospheric Pressure and 180° C.

DMC was prepared in the same manner as in Example 1, except that CaO, MgO, PbO, and hydrotalcite [Mg$_5$Al (OH)$_{12}$(CO$_3$)$_{0.5}$·4H$_2$O] and an impregnated catalyst containing 20% by weight of ZnO and 80% by weight of TiO$_2$ were used as catalysts instead of ZnO catalyst. The yields and the selectivity according to the reaction times of the prepared DMC were shown in the following table 1:

TABLE 1

| | | DMC Analysis | | | | | |
|---|---|---|---|---|---|---|---|
| | | After 2.5 hours of Reaction | | After 6.5 hours of Reaction | | After 10.5 hours of Reaction | |
| Examples | Catalysts | Yield (%) | Selectivity (%) | Yield (%) | Selectivity (%) | Yield (%) | Selectivity (%) |
| Example 1 | ZnO | 23.1 | 89.4 | 26.3 | 94.9 | 38.8 | 97.4 |
| Example 1-1 | ZnO | 9.3 | 33.6 | 21.1 | 69.0 | 28.1 | 83.5 |
| Example 2 | CaO | 17.6 | 80.6 | 22.6 | 85.4 | 28.3 | 91.3 |
| Example 3 | MgO | 26.4 | 84.1 | 30.8 | 89.8 | 39.9 | 94.5 |
| Example 4 | PbO | 11.1 | 60.8 | 37.9 | 91.6 | 53.2 | 95.5 |
| Example 5 | Y$_2$O$_3$ | 13.1 | 61.4 | 20.3 | 75.3 | 29.4 | 85.4 |
| Example 6 | La$_2$O$_3$ | 6.1 | 53.7 | 7.6 | 50.6 | 12.6 | 58.1 |
| Example 7 | Hydrotalcite[1] | 34.3 | 88.6 | 46.5 | 95.3 | 39.4 | 85.5 |
| Example 8 | Hydrotalcite[2] | 16.4 | 82.7 | 24.0 | 90.9 | 25.2 | 94.2 |

TABLE 1-continued

| | | DMC Analysis | | | | | |
|---|---|---|---|---|---|---|---|
| | | After 2.5 hours of Reaction | | After 6.5 hours of Reaction | | After 10.5 hours of Reaction | |
| Examples | Catalysts | Yield (%) | Selectivity (%) | Yield (%) | Selectivity (%) | Yield (%) | Selectivity (%) |
| Example 9 | 20 wt % ZnO 80 wt % $TiO_2$ | 11.9 | 68.5 | 23.3 | 82.7 | 20.2 | 84.4 |

[1] Hydrotalcite: $Mg_5Al(OH)_{12}(CO_3)_{0.6} \cdot 4H_2O$ dried at 120° C. for 12 hours
[2] Hydrotalcite: $Mg_5Al(OH)_{12}(CO_3)_{0.6} \cdot 4H_2O$ calcined at 450° C. for 6 hours Examples 10 to 15 & Comparative Examples 1 to 4

Preparation of DMC Using Different Ionic Liquid

DMC was prepared in the same manner as in Example 1, except that the kind of ionic liquids was changed, and the yields and the selectivities of the prepared DMCs are shown in the following table 2:

active sites of a solid catalyst. As a result, it was shown that the [Betain][NTf$_2$] exhibited low yield and low selectivity of DMC. The ionic liquids having a tetrafluoroborate (BF$_4$) or hexafluorophosphate (PF$_6$) anion in Comparative Examples 2 to 4 exhibited very low reactivities of DMC. Moreover, the tetrafluoroborate and hexafluorophosphate were reacted with methanol as a reactant to produce by-products such as tri-methoxyboroxane and methoxy phosphorus compounds, which reduces the selectivity to DMC and generates hydrofluoric acid (HF) to corrode the reactor.

TABLE 2

| | | DMC Analysis | | | | | |
|---|---|---|---|---|---|---|---|
| | | After 2.5 hours of Reaction | | After 6.5 hours of Reaction | | After 10.5 hours of Reaction | |
| Examples | Ionic liquids | Yield (%) | Selectivity (%) | Yield (%) | Selectivity (%) | Yield (%) | Selectivity (%) |
| Example 1 | [Choline][NTf$_2$] | 23.1 | 89.4 | 26.3 | 94.9 | 38.8 | 97.4 |
| Example 10 | [HEMin][NTf$_2$] | 13.3 | 88.9 | 18.2 | 94.4 | 21.1 | 95.9 |
| Example 11 | [EMin][NTf$_2$] | 9.6 | 54.5 | 15.7 | 76.8 | 15.7 | 80.4 |
| Example 12 | [HETEA][NTf$_2$] | 16.6 | 93.1 | 18.1 | 96.6 | 19.6 | 98.1 |
| Example 13 | [HETBA][NTf$_2$] | 22.1 | 84.3 | 27.0 | 93.4 | 28.2 | 94.1 |
| Example 14 | [TEA][NTf$_2$] | 10.0 | 55.0 | 14.1 | 72.2 | 16.5 | 79.6 |
| Example 15 | [TBA][NTf$_2$] | 11.8 | 64.2 | 15.8 | 67.9 | 20.5 | 75.5 |
| Comparative Example 1 | [Betain][NTf$_2$] | 0.3 | 16.4 | 0.8 | 15.3 | 0.8 | 23.2 |
| Comparative Example 2 | [Choline][BF$_4$] | 0 | 0 | 0 | 0 | 0.1 | 16.4 |
| Comparative Example 3 | [BMin][BF$_4$] | 1.4 | 0.2 | 1.9 | 0.2 | 2.6 | 0.2 |
| Comparative Example 4 | [BMin][PF$_6$] | 0.1 | 0 | 0.3 | 0 | 0.3 | 0.01 |

[Choline][NTf$_2$]: hydroxyethyltrimethylammonium bis(trifluoromethylsulfonyl)imide
[HEMin][NTf$_2$]: 1-hydroxyethyl-3-methyl-imidazolium bis(trifluoromethylsulfonyl)imide
[EMin][NTf$_2$]: 1-ethyl-3-methyl-imidazolium bis(trifluoromethylsulfonyl)imide
[HETEA][NTf$_2$]: hydroxyethyltriethylammonium bis(trifluoromethylsulfonyl)imide
[HETBA][NTf$_2$]: hydroxyethyltributylammonium bis(trifluoromethylsulfonyl)imide
[TEA][NTf$_2$]: tetraethylammonium bis(trifluoromethylsulfonyl)imide
[TBA][NTf$_2$]: tetrabutylammonium bis(trifluoromethylsulfonyl)imide
[Betain][NTf$_2$]: 1-carboxy-N,N,N-trimethylmethanaminium hydroxide bis(trifluoromethylsulfonyl)imide
[Choline][BF$_4$]: hydroxyethyltrimethylammonium tetrafluoroborate
[BMin][BF$_4$]: 1-butyl-3-methyl-imidazolium tetrafluoroborate
[BMin][PF$_6$]: 1-butyl-3-methyl-imidazolium hexafluorophosphate

[Betain][NTf$_2$] in Comparative Example 1 is an ionic liquid having a carboxyl cation which produces a hydrogen ion (H$^+$) but dissolves the metal oxide catalyst to deactivate the However, it was confirmed that the DMC prepared in Examples 1, and 9 to 14 using the ionic liquids provided by the present invention had high yields and high selectivities.

Comparative Examples 5 to 8

Preparation of DMC Using PGDE Solvent

DMC was prepared in the same manner as in Example 1, except that 100 g of polyethylene glycol dimethyl ether (PGDE, MW 250 to 270) as a high boiling electron donor organic compound was used instead of the ionic liquid and different catalysts were used. The yields and selectivities of the thus prepared DMC are shown in the following table 3:

TABLE 3

| | | DMC Analysis | | | | | |
|---|---|---|---|---|---|---|---|
| | | After 2.5 hours of Reaction | | After 6.5 hours of Reaction | | After 10.5 hours of Reaction | |
| Comparative Examples | Catalysts | Yield (%) | Selectivity (%) | Yield (%) | Selectivity (%) | Yield (%) | Selectivity (%) |
| Comparative Example 5 | ZnO | 8.4 | 0.02 | 12.4 | 0.02 | 12.2 | 0.02 |
| Comparative Example 6 | $TiO_2$ | 0.11 | 0.00 | 0.11 | 0.00 | 0.16 | 0.00 |
| Comparative Example 7 | $C_{66}H_{70}O_4Zn$* | 0.0 | 0.00 | 0.38 | 0.00 | 0.72 | 0.00 |
| Comparative Example 8 | $C_{66}H_{70}O_4Zn$ | 1.03 | 0.00 | 1.58 | 0.00 | 1.66 | 0.00 |

*reaction temperature (150° C.)

It can be seen from Table 3 that the yields with respect to the amount of urea added were all low except for those in Comparative Example 5 using the zinc oxide catalyst and the selectivities were very bad due to an increase in impurities. The reason for this is considered that the high boiling solvent PGDE was decomposed at the reaction temperature of 180° C. and distilled with a significant amount of low molecular by-products together with a condensate, thus reducing the selectivity, which considerably increases the cost of purification thus having no economical advantage.

Examples 16 and 17

Preparation of Diethyl Carbonate and di-n-propyl Carbonate at Atmospheric Pressure and 180° C.

Diethyl carbonate and di-n-propyl carbonate were prepared in the same manner as in Example 1, except that ethyl alcohol and 1-propyl alcohol were used instead of methanol and a solution having a molar ratio of ethanol (or n-propanol) to urea of 10:1 was prepared and injected at a constant flow rate of 0.5 ml/min. The results obtained are shown in the following table 4:

TABLE 4

| | | DMC Analysis | | | | | |
|---|---|---|---|---|---|---|---|
| | | After 2.5 hours of Reaction | | After 6.5 hours of Reaction | | After 10.5 hours of Reaction | |
| Examples | Dialkyl carbonates | Yield (%) | Selectivity (%) | Yield (%) | Selectivity (%) | Yield (%) | Selectivity (%) |
| Example 16 | diethyl carbonate | 10.9 | 94.3 | 15.5 | 96.0 | 17.6 | 98.3 |
| Example 17 | di-n-propyl carbonate | 8.8 | 67.6 | 12.4 | 79.8 | 13.0 | 95.8 |

It can be seen from Table 4 that it was possible to obtain good yields of more than 13% and dialkyl carbonate of high purity containing no impurities other than the intermediate products such as ethyl carbamate and n-propyl carbamate even in the reactions using ethyl alcohol and 1-propyl alcohol.

Examples 18 to 20

Preparation of DMC at Different Temperatures

DMC was prepared in the same manner as in Example 4, except that a metal oxide catalyst (PbO) was used at different temperatures and the analysis results are shown in the following table 5:

TABLE 5

| | | DMC Analysis | | | | | |
|---|---|---|---|---|---|---|---|
| | | After 2.5 hours of Reaction | | After 6.5 hours of Reaction | | After 10.5 hours of Reaction | |
| Examples | Temp. (° C.) | Yield (%) | Selectivity (%) | Yield (%) | Selectivity (%) | Yield (%) | Selectivity (%) |
| Example 18 | 160 | 3.0 | 50.4 | 3.7 | 50.6 | 5.4 | 53.0 |
| Example 4 | 180 | 11.1 | 60.8 | 37.9 | 91.6 | 53.2 | 95.5 |
| Example 19 | 200 | 37.4 | 85.6 | 38.6 | 94.4 | 32.0 | 95.6 |
| Example 20 | 220 | 27.1 | 80.9 | 12.5 | 89.3 | 6.7 | 91.8 |

When the reaction temperature was 160° C., the yield and selectivity of DMC were low due to the MC synthesized by the first step reaction. However, since no other impurities were produced, it was possible to increase the yield of DMC by recirculating MC and methanol remaining in the reboiler after azeotropic distillation of DMC and methanol. Meanwhile, when the reaction temperature was 220° C., the N-methyl carbamate was produced as a by-product by the reaction of DMC and MC after 2.5 hours of the reaction, and thus the selectivity was gradually decreased. Even in this case, it is possible to increase the productivity by an increase in the reaction rate if the MC and methanol remaining in the reboiler are recirculated after collecting the produced DMC by azeotropic distillation.

Examples 21 to 24

Preparation of DMC in Different Amounts of Catalyst at Atmospheric Pressure and 180° C.

DMC was prepared in the same manner as in Example 3, except that the amount of MgO catalyst used was changed as shown in the following table 6:

TABLE 6

| | | | DMC Analysis | | | | | |
|---|---|---|---|---|---|---|---|---|
| | | | After 2.5 hours of Reaction | | After 6.5 hours of Reaction | | After 10.5 hours of Reaction | |
| Examples | Ionic liquid | Amount Of catalyst | Yield (%) | Selectivity (%) | Yield (%) | Selectivity (%) | Yield (%) | Selectivity (%) |
| Example 21 | [choline][NTf$_2$] | 0.5 | 21.5 | 79.8 | 26.8 | 87.6 | 28.6 | 91.6 |
| Example 22 | | 1.0 | 23.1 | 82.8 | 29.5 | 91.4 | 31.8 | 94.3 |
| Example 3 | | 2.0 | 26.4 | 84.1 | 30.8 | 89.6 | 39.9 | 94.5 |
| Example 23 | | 3.0 | 23.4 | 83.7 | 31.6 | 92.8 | 30.5 | 94.7 |
| Example 24 | | 4.0 | 26.9 | 87.4 | 32.7 | 94.7 | 33.5 | 96.6 |

Examples 25 to 29

Preparation of DMC in Different Amounts of Urea Under Atmospheric Pressure and at 180° C.

DMC was prepared in the same manner as in Example 1, except that the amount of urea used was changed and a ZnO catalyst dried at 120° C. for 12 hours was used. The yields and selectivities of DMC are shown in the following table 7:

TABLE 7

| | | | DMC Analysis | | | | | |
|---|---|---|---|---|---|---|---|---|
| | | Molar ratio of | After 2.5 hours of Reaction | | After 6.5 hours of Reaction | | After 10.5 hours of Reaction | |
| Examples | Amount of urea | methanol to urea | Yield (%) | Selectivity (%) | Yield (%) | Selectivity (%) | Yield (%) | Selectivity (%) |
| Example 25 | 5.623 | 20.0 | 20.3 | 90.0 | 19.6 | 95.6 | 20.3 | 93.4 |
| Example 26 | 6.426 | 17.5 | 17.2 | 87.4 | 24.9 | 95.0 | 23.8 | 95.2 |
| Example 1 | 7.500 | 15.0 | 23.1 | 89.4 | 26.3 | 94.9 | 38.8 | 97.4 |
| Example 27 | 8.996 | 12.5 | 14.9 | 88.2 | 22.0 | 94.3 | 21.9 | 93.6 |
| Example 28 | 11.245 | 10.0 | 16.7 | 85.0 | 16.9 | 87.5 | 24.4 | 92.8 |
| Example 29 | 14.994 | 7.5 | 10.0 | 60.5 | 16.2 | 74.5 | 17.5 | 78.2 |

The above results were obtained by varying the molar ratio of methanol to urea relative to 100 g of the ionic liquid. When the amount of urea used was in the range of 5 to 15 g, there was no significant change in the yield. When the amount of urea used was large, the concentration of MC as an intermediate product was increased, thereby decreasing the selectivities. Meanwhile, when the amount of urea used was small, there was no significant change in the yield and selectivity, but the productivity was reduced, thus not being economical.

Examples 30 to 34

Preparation of DMC at Different Flow Rates of Methanol and Urea Fed at the Same Time DMC was prepared in the same manner as in Example 1, except that a solution prepared by dissolving 7.5 g of urea in 60 g of methanol (molar ratio of methanol to urea was 15:1) was fed into the reactor at different flow rates as shown in the following table 8:

TABLE 8

| Examples | Flow rate (ml/min) | Reaction temp. | DMC Analysis | | | | | |
|---|---|---|---|---|---|---|---|---|
| | | | After 2.5 hours of Reaction | | After 6.5 hours of Reaction | | After 10.5 hours of Reaction | |
| | | | Yield (%) | Selectivity (%) | Yield (%) | Selectivity (%) | Yield (%) | Selectivity (%) |
| Example 30 | 0.25 | 180° C. | 0.5 | 100 | 8.8 | 96.8 | 27.1 | 94.5 |
| Example 31 | 0.5 | | 5.7 | 85.1 | 16.3 | 80.0 | 18.1 | 86.0 |
| Example 32 | 1.0 | | 15.0 | 68.1 | 18.0 | 71.7 | 21.2 | 49.9 |
| Example 33 | 2.0 | | 10.0 | 61.2 | 12.3 | 48.5 | 12.7 | 49.9 |
| Example 34 | 3.0 | | 10.6 | 38.9 | 13.4 | 46.2 | 14.2 | 42.7 |

As shown in Examples 30 to 34, the yield and selectivity of DMC were related to the flow rate. At high flow rate of methanol was shown closely related to factors such as the type of the disperser of methanol vapor in the reactor, and contact time of reactants in the ionic liquid. Therefore, the decrease in the yield and selectivity is ascribed to the following reasons. That is, the gaseous methanol of the reactant was not smoothly dispersed and its contact time with the reactants was not sufficient due to the high flow rate, thus reducing the yield of DMC, and the selectivity was reduced due to MC synthesized by the first step of the reaction.

However, it is possible to increase the yield of DMC by redistilling the produced condensate to obtain an azeotropic mixture of 30% by weight of DMC and 70% by weight of MeOH at 62.7° C. and re-circulate the methanol and MC remaining in the reboiler.

In the present invention, when the flow rate is low, the yield by using the ionic liquid slurry catalyst system is increased but the productivity is reduced. On the contrary, when the flow rate is increased, the yield is reduced but the productivity is increased if the methanol and MC are re-circulated by the distillation system employed. However, a significant increase or decrease in the flow rates reduces the yield and the productivity, which is undesirable. Therefore, in the present invention, alkyl alcohol may be fed at a flow rate of 0.1 to 10 ml/min, preferably at a flow rate of 0.1 to 5 ml/min, more preferably 0.1 to 3 ml/min; however, the present invention is not limited thereto.

The conventional methods for preparing dialkyl carbonates have the problems that the amount of energy required for the separation and purification of the products is increased owing to the amount of by-products produced at high temperature and high pressure. Moreover, since the concentration of the produced DMC is lower than that at atmospheric pressure due to a change in the boiling point at high pressure when the synthesis is performed by the reactive distillation, the productivity is reduced and the energy cost is increased due to the recirculation of methanol as a raw material. Further, when the reaction pressure is high, the cost of equipment for safety is increased, and the cost of a pressure control device required to control the pressure is also increased. As such, there are many problems that the reaction yield or selectivity is low due to the by-products such as N-MC and NN-DMC, the cost of equipment is increased, and a large amount of energy is required due to the complicated process and high pressure.

However, as can be confirmed from the above-described Examples, the present invention can prepare dialkyl carbonate at atmospheric pressure with high yield and selectivity. Therefore, since the present invention does not require expensive pressure control device and peripheral devices for maintaining high pressure, it is possible to reduce the installation cost and prepare dialkyl carbonate with high yield, thus improving the cost effectiveness.

Moreover, since the used ionic liquid can be easily recycled by purification and there is hardly no waste produced thereof, the method for preparing dialkyl carbonate of the present invention is an environment-friendly method.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A method for preparing dialkyl carbonate by reacting alkyl alcohol with urea or alkyl carbamate in the presence of: an ionic liquid comprising a cation capable of generating a hydrogen ion (H+), and a hydrophobic anion containing fluorine, and a catalyst,
   wherein said cation is a quaternary ammonium cation, an imidazolium cation, a pyridium cation, a pyrazolium cation, a pyrrolinium cation, a quaternary phosphonium cation, a thiazolium cation, or a sulfonium cation, and said hydrophobic anion is bis(trifluoromethylsulfonyl)imide, trifluoromethanesulfonate, or tris(trifluoromethylsulfonyl)methanide.

2. The method for preparing dialkyl carbonate according to claim 1, wherein the quaternary ammonium cation contains at least one substituent selected from the group consisting of a $C_1$-$C_5$ hydroxyalkyl group, a $C_1$-$C_5$ alkoxy group, and a $C_1$-$C_5$ alkyl group.

3. The method for preparing dialkyl carbonate according to claim 2, wherein the quaternary ammonium cation is a hydroxymethyltrimethylammonium cation, a hydroxyethyltrimethylammonium cation, a hydroxyethyltriethylammonium cation, a hydroxyethyltripropylammonium cation, a hydroxyethyltributylammonium cation, a tetraethylammonium cation, or a tetrabutylammonium cation.

4. The method for preparing dialkyl carbonate according to claim 3, wherein the imidazolium cation is a 1,3-di($C_1$-$C_5$)alkyl-imidazolium cation or a 1-hydroxy($C_1$-$C_5$)alkyl-3-($C_1$-$C_5$)alkyl imidazolium cation.

5. The method for preparing dialkyl carbonate according to claim 1, wherein the hydrophobic anion is bis(trifluoromethylsulfonyl)imide.

6. The method for preparing dialkyl carbonate according to claim 1, wherein the ionic liquid is [ethyltrimethylammonium][bis(trifluoromethylsulfonyl)imide], [hydroxyethyltriethylammonium][bis(trifluoromethylsulfonyl)imide], [1-hydroxyethyl-3-methyl-imidazolium][bis(trifluoromethylsulfonyl)imide], or [1-ethyl-3-methylimidazolium][bis(trifluoromethylsulfonyl)imide].

7. The method for preparing dialkyl carbonate according to claim 1, wherein the catalyst comprises at least one selected from the group consisting of CaO, MgO, ZnO, PbO, $La_2O_3$, $Y_2O_3$ and hydrotalcite.

8. The method for preparing dialkyl carbonate according to claim 1, wherein the catalyst is used in an amount of 1 to 10 parts by weight per 100 parts by weight of the ionic liquid.

9. The method for preparing dialkyl carbonate according to claim 1, wherein the urea or alkyl carbamate is used in an amount of 1 to 30 parts by weight per 100 parts by weight of the ionic liquid and the alkyl alcohol is used in a molar ratio of 5 to 25 per mole of the urea or alkyl carbamate.

10. The method for preparing dialkyl carbonate according to claim 1, wherein the reaction is carried out in a temperature range from 140 to 240° C.

11. The method for preparing dialkyl carbonate according to claim 10, wherein the reaction pressure is carried out below a saturated vapor pressure of alkyl alcohol or atmospheric pressure at reaching the reaction temperature.

12. The method for preparing dialkyl carbonate according to claim 10, wherein the reaction is carried out at or below atmospheric pressure.

13. A method for preparing dialkyl carbonate by reacting alkyl alcohol with urea or alkyl carbamate in the presence of: an ionic liquid comprising a cation capable of generating a hydrogen ion (H+), and a hydrophobic anion containing fluorine, and a catalyst, wherein said cation is a hydroxymethyltrimethylammonium cation, a hydroxyethyltrimethylammonium cation, a hydroxyethyltriethylammonium cation, a hydroxyethyltripropylammonium cation, a hydroxyethyltributylammonium cation, a tetraethylammonium cation, or a tetrabutylammonium cation, and said hydrophobic anion is bis(trifluoromethylsulfonyl)imide.

14. The method for preparing dialkyl carbonate according to claim 13, wherein the ionic liquid is [ethyltrimethylammonium][bis(trifluoromethylsulfonyl)imide], [hydroxyethyltriethylammonium][bis(trifluoromethylsulfonyl)imide], [1-hydroxyethyl-3-methyl-imidazolium][bis(trifluoromethylsulfonyl)imide], or [1-ethyl-3-methylimidazolium][bis(trifluoromethylsulfonyl)imide].

15. The method for preparing dialkyl carbonate according to claim 13, wherein the catalyst comprises at least one selected from the group consisting of CaO, MgO, ZnO, PbO, $La_2O_3$, $Y_2O_3$ and hydrotalcite.

16. The method for preparing dialkyl carbonate according to claim 13, wherein the catalyst is used in an amount of 1 to 10 parts by weight per 100 parts by weight of the ionic liquid.

17. The method for preparing dialkyl carbonate according to claim 13, wherein the urea or alkyl carbamate is used in an amount of 1 to 30 parts by weight per 100 parts by weight of the ionic liquid and the alkyl alcohol is used in a molar ratio of 5 to 25 per mole of the urea or alkyl carbamate.

18. The method for preparing dialkyl carbonate according to claim 13, wherein the reaction is carried out in a temperature range from 140 to 240° C.

19. The method for preparing dialkyl carbonate according to claim 18, wherein the reaction pressure is carried out below a saturated vapor pressure of alkyl alcohol or atmospheric pressure at reaching the reaction temperature.

20. The method for preparing dialkyl carbonate according to claim 18, wherein the reaction is carried out at or below atmospheric pressure.

* * * * *